United States Patent [19]

Mühlemann et al.

[11] Patent Number: 4,828,822

[45] Date of Patent: May 9, 1989

[54] PROCESS FOR STABILIZING AQUEOUS COMPOSITIONS CONTAINING TIN SALTS

[75] Inventors: Hans R. Mühlemann, Zollikon; Hans Schmid, Muttenz, both of Switzerland

[73] Assignee: GABA International AG, Basel, Switzerland

[21] Appl. No.: 109,830

[22] Filed: Oct. 16, 1987

Related U.S. Application Data

[63] Continuation-in-part of Ser. No. 363,013, Mar. 29, 1982, abandoned, which is a continuation of Ser. No. 192,874, Oct. 1, 1980, abandoned.

[30] Foreign Application Priority Data

| Oct. 2, 1979 [GB] | United Kingdom | 7934159 |
| Jan. 24, 1980 [GB] | United Kingdom | 8002433 |
| Feb. 1, 1980 [GB] | United Kingdom | 8003525 |

[51] Int. Cl.⁴ .................. A61K 7/16; A61K 7/18; A61K 7/22
[52] U.S. Cl. ........................................... 424/52; 424/54
[58] Field of Search .................................. 424/52, 54

[56] References Cited

U.S. PATENT DOCUMENTS

| 3,083,143 | 3/1963 | Schmid et al. |
| 3,105,013 | 9/1963 | Saul et al. |
| 3,277,118 | 10/1966 | Schmid et al. |
| 3,282,792 | 11/1966 | Fiscella |
| 3,413,326 | 11/1968 | Schmid |
| 3,445,567 | 5/1969 | Muhler |
| 3,544,678 | 12/1970 | Griebstein |
| 3,914,406 | 10/1975 | Yankell |
| 3,932,604 | 1/1976 | Barth |
| 3,970,747 | 7/1976 | Barth |
| 4,088,752 | 5/1978 | Muhlemann et al. |
| 4,117,109 | 9/1978 | Stookey |
| 4,157,386 | 6/1979 | La Rochelle |
| 4,279,888 | 7/1981 | Suganuma et al. |
| 4,308,252 | 12/1981 | Tomaich et al. |
| 4,308,253 | 12/1981 | Schmid et al. |

FOREIGN PATENT DOCUMENTS

| 969862 | 6/1975 | Canada |
| 865272 | 4/1961 | United Kingdom |
| 869257 | 5/1962 | United Kingdom |
| 1003595 | 9/1965 | United Kingdom |
| 1066795 | 4/1967 | United Kingdom |
| 1067352 | 5/1967 | United Kingdom |
| 1194885 | 6/1970 | United Kingdom |
| 1249742 | 10/1971 | United Kingdom |
| 1272454 | 4/1972 | United Kingdom |
| 1381826 | 1/1975 | United Kingdom |
| 1475899 | 6/1977 | United Kingdom |
| 2007974A | 10/1978 | United Kingdom |

OTHER PUBLICATIONS

Chemical Abstract, 108480j, Toxicological Aspects of Stannous Fluoride after Ingestion as a Clear, Precipitate-Free Solution Compared to Sodium Fluoride.

S. Ebell, "Karies und Zuckeraustauschstoffe", Emahrungsclorschung Hett, 1978, pp. 171-174.

H. R. Muhlemann, "Zuckerfreie, Zahnschonende und Nicht-Kariogene Bonbons und Sussigkeiten".

88, Scand J. Dent. Res., 193-200 (1980), "Effect of Mouthrinses With Tin (II), Fluoride, Lanthanum Chloride, Sodium Fluoride and Chlorohexidine on the Amount of Lipoteichoic Acid Formed in Plaque".

Substitution of Sucrose by Lycasin in Candy, Roslagen Study, Frostell et al., Acta Odontol. Scand., 1974, 32(4), 235-54 (Eng.), 71769m, CA 82-71769.

Chemical Abstract, 80-128408h, Effect of Mouth Rinses with Sucrose, Glucose, Fructose, Lactose, Sorbitol, and Lycasin on the pH of Dental Plaque.

Chemical Abstracts, 93-106820c, Effect of Inorganic Ions and Surface Active Organic Compounds on the Adherence of Oral Streptococci.

Chemical Abstract, 93:43218q, Relation of Amylase to Starch and Lycasin Metabolism in Human Dental Plaque in Vitro.

Fed. Reg. 17,245(1974).

Chemical Abstract, 93:143814Z, Effect of Mouthrinses with Tin (II), Fluoride, Lanthanum Chloride, Sodium Fluoride, and Chlorhexidine on the Amount of Lipoteichoic Acid Formed in Plaque.

Chemical Abstract, 93-143813y, Effect on low pH and Fluoride Levels Upon Growth and Sugar Catabolism by Plaque Bacteria.

Chemical Abstract, 163957s, Mouthwash Compositions Containing Maltitol.

Chemical Abstract, 91:90089s, Effects of 3 Months Frequent Consumption of Hydrogenated Starch Hydrolyzate (Lycasin), Maltitol, Sorbitol and Xylitol on Human Dental Plaque.

Chemical Abstract, 91:54724m, Acid Production from Sucrose Substitutes in Human Dental Plaque.

Chemical Abstract, 89:195886m, Acid Production from Swedish Lycasin (Candy Quality) and French Lycasin (80/55), in Human Dental Plaques.

Chemical Abstract, 93:184332j, Lycasin Hydrogenated Hydrolyzates.

Chemical Abstracts, 91:Spalte 417v, An In Vivo Study of the Effects of Fluoride (Stannous Fluoride 0.4%, APF 1.23%, and Neutral Sodium Fluoride 0.05%) on Levels of Organisms Resembling Actnomyces, Gingival Inflamation and Plaque Accumulation.

Chemical Abstract, 91-73170u, Technological Problems in the Incorporation of Hydrogenated Glucose Syrups and L-Sorbose.

Chemical Abstracts, 88-47350w, Acid Production from Lycasin, Maltitol, Sorbitol and Xylitol by Oral Streptococci and Lactobacilli.

Chemical Abstracts, 81-54360h, Topical Fluoride Preparations for Reducing Incidence of Dental Caries.

Chemical Abstract, 76-57450v, Effects of Sucrose, Starch, and a Hydrogenated Starch Derivateive on Dental Caries in the Rat.

Chemical Abstract, 75-74793f, Effects of Consumption of Hydrogenated Saccharides and Sucrose on the Blood Sugar Concentration.

Chemical Abstract, 92-35405n, Contribution of Maltitol and Lycasin to Experimental Enamel Demineralization in the Human Mouth.

Topical Fluoride Preparations for Reducing Incidence of Dental Caries Notice of Status, 63–Pharmaceuticals, Robert Doerge, 54360h.

*Primary Examiner*—Shep K. Rose
*Attorney, Agent, or Firm*—Finnegan, Henderson, Farabow, Garrett & Dunner

[57] ABSTRACT

Formulations for oral care and dental care, which contain tin (II) salts and water, are stabilized against hydrolysis of the tin salts by the addition of certain cationic surfactant diamine salts. The additive fully preserves, or even potentiates, the inhibiting action of tin salts on plaque formation an dental caries. The formulations advantageously also contain a non-ionic, water-soluble addition product of ethylene oxide which further improves the stability.

6 Claims, No Drawings

PROCESS FOR STABILIZING AQUEOUS COMPOSITIONS CONTAINING TIN SALTS

The invention relates to a process for stabilizing oral compositions for the prophylaxis and combating of plaque formation and of dental caries, which compositions contain one or more tin (II) salts in a water containing medium, and whose stability over a lengthy period is ensured through stabilisation of the tin salt(s). The term oral compositions in particular embraces tooth-pastes, dental gels, mouthwashes, mouth sprays, rinsing tablets, prophylaxis pastes, solutions for local application, and the like.

The tin(II) ions have a plaque-inhibiting action; this action has been demonstrated in dogs, for local application, and in man, for the use of mouthwashes containing SnF2. It has also been found that mouthwashes containing SnF2 at a concentration corresponding to 780 and 3,100 ppm of $Sn^{++}$ reduce the formation of acid from sucrose in the bacterial deposits. SnF2 is generally recognised by scientific circles as an agent for combating dental caries, and is an effective constituent of caries-inhibiting preparations.

The metabolic effects of low SnF2 concentrations in counteracting plaque are in the main attributable to the antibacterial action of the tin(II) ions, which probably cause changes in the cell membranes of the bacteria. It has also been found that the reduction in plaque under the action of tin(II) ions is accompanied by a regression of gingivitis.

In practical respects, however, it is an important disadvantage that tin(II) salts, inter alia tin(II) fluoride, rapidly decompose in oral preparations diluted with water; this is true in particular for the low concentration ranges and at the pH values acceptable in the mouth (pH from about 4.5 to 9.0), such as are encountered in mouthwashes, rinsing solutions, toothpastes and other formulations for the care of the mouth and of the teeth. Freshly prepared solutions of tin(II) fluoride or of tin-(II) chloride and an alkali metal fluoride show opalescence and turbidity within from one to 10 minutes. When the solutions are left to stand, white precipitates subsequently form, and these progressively increase in amount over a period of 3 to 7 days [Accepted Dental Therapeutics, 36th edition, Amer. Dent. Ass., Chicago (IL, USA) 1975]. The formation of insoluble precipitates, such as the sparingly soluble tin(II) hydroxide, $Sn(OH)_2$, is caused by hydrolysis and oxidation of the unstable divalent tin ions. The formation of precipitates from the solutions of tin(II) chloride or fluoride correspondingly reduces the protective action of the tin ions on the teeth, and the plaque-inhibiting action of the tin ions [I.L. Shannon, J. Southern Calif. State Dent. Ass. 32 (1964), 67]. The loss of titratable tin(II) ions in dilute (0.157% strength) SnF2 solutions has been reported on, with examples [J.K. Lim, J. Dent. Res. 49 (1970), 760]: The concentration of tin ions fell, after 1, 2, 5 and 7 days, by, respectively, 8.1, 14.8, 36.3 and 48.4%. A similar reduction in the concentration of tin(II) ions has also been observed in ageing SnF2 toothpastes.

In the preparation of aqueous formulations for the care of the mouth and the teeth, numerous attempts have already been made to prevent the precipitation of the tin ions. The methods for the "stabilisation" of the tin(II) fluoride include the dissolution in water, immediately prior to use, of solid tin(II) fluoride contained in hard gelatin capsules, thereby ensuring that a fresh and effective mouth rinse is produced [P.E. Norris, J. Amer. Pharm. Ass. 20 (1959), 86]. Fresh rinsing solutions can also be prepared, immediately prior to use, from SnF2 tablets or by dilution of highly concentrated and more stable 20% strength SnF2 solutions [I.L. Shannon and colleagues, J. Southern Calif. State Dent. Ass. 33 (1965), 520].

Long-lasting stability has been achieved by incorporating tin(II) fluoride into anhydrous glycerol [I.L. Shannon, Caries Res. 3 (1969), 339].

Aqueous solutions of tin(II) fluoride containing added sodium fluoride, glycerol or tartaric acid at appropriate concentrations can, for a limited period of time, be kept in a clear, precipitate-free and esthetically acceptable condition at room temperature and at an elevated temperature. However, the concentration of tritratable tin(II) ions proves to be greatly reduced by the additives [J.K. Lim, loc. cit. and J. Dent. Res. 50 (1971), 531].

Viewed overall, the numerous attempts to stabilise the aqueous solutions of tin(II) fluoride have only produced a small partial success, namely through the preparation of mouthwashes immediately prior to use [Anon, Federal Register 39 (1974), 17245]. On the other hand, in conventional formulations for the care of the mouth and the teeth, which formulations are required to withstand, without damage, at least a certain period of storage, the problem has hitherto remained unsolved.

Further attempts to stabilize oral aqueous compositions containing a stannous salt comprise adding an orally acceptable acid such that the pH of the composition is in the range of from 2 to 4, i.e. the composition is in substantially acidic state (GB 2,007,974, Y. Ochiai et al.), or adding as a complexing agent hydroxyethylnitrilodiacetic acid, m-hydroxybenzoic acid, 1,2,3-propanetricarboxylic acid or itaconic acid (U.S. Pat. No. 3,544,678, W.J. Griebstein). As further complexing agents of the same kind, hydroxyl substituted aliphatic di- and tri-carboxylic acids like malic acid and citric acid also may be used for stabilisation of SnF2 in aqueous compositions (U.S. Pat. No. 3,282,792, A.J. Fiscella).

It has now been found, surprisingly, that the addition of certain water-soluble organic diamine salts to aqueous media which contain tin(II) fluoride, other tin(II) salts or mixtures of fluorine-free tin salts with fluorides of other metals, usually, at a tin concentration of 0.005 to 0.5% by weight, permits the preparation of stable, precipitate-free formulations for the care of the mouth and of the teeth.

When tin(II) fluoride is used, the concentration should advantageously be within the range of 0.04 to 0.6% by weight of SnF2. Solutions of tin(II) fluoride are stabilised by the addition of one or more water-soluble organic amine salts in a weight ratio of Sn : amine which is suitably from 1:10 to 10:1. Preferably, the two components are employed in equimolar concentration. This gives mixtures which for several months at room temperature remain clear and free from tin precipitates and in which the action of the tin(II) fluoride against plaque and against gingivitis does not suffer.

Accordingly, the present invention provides a process for stabilizing oral compositions consisting essentially of water and at least one tin (II) salt, which process comprises adding to said compositions at least one diamine salt which is a cationic surfactant in a sufficient amount to stabilize the tin salt(s). Advantageously, these formulations additionally contain fluoride ions.

Tin salts which can be employed are, in particular, tin(II) fluoride, chloride, bromide, sulfate or tartrate. Accordingly, tin(II) fluoride in particular, preferably in a concentration of 0.05 to 0.5% by weight of Sn, will tend to be used, or the tin ions will be added in the form of a fluorine-free tin salt, such as the other tin salts mentioned above, but in that case advantageously in conjunction with sodium fluoride, potassium fluoride, ammonium fluoride or fluorides of other metals.

Suitable diamine salts which are cationic surfactants have been described, inter alia, in German Patent Specification No. 1,198,493 and U.S. Pat. Spec. Nos. 3,083,143 and 4,088,752.

Amongst the compounds which have proved very particularly suitable are aliphatic tertiary diamines which have one alkyl group derived from a fatty acid and two polyoxyethylene groups bonded to the nitrogen atom and containing a total of 20 to 50 ethyleneoxy groups, in particular compounds of the formula:

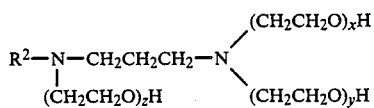

wherein $R^2$ denotes a fatty alkyl group with 7 to 19 carbon atoms and x, y and z each denote an integer from 1 onwards, preferably from 1 to 10. These compounds are used in the form of their salts with inorganic or organic acids. A typical example of such a compound is N,N,N'-tris-(2-hydroxyethyl)-N'-octadecyl-1,3-diaminopropane, which, in the form of the dihydrofluoride, is referred to as amine fluoride 297 and abbreviated to AmF 297 [H.R. Muhlemann, Quintessenz 18 (1976), Nos. 5–8].

Suitable acid components of the amine salt are all acids which impart solubility in water to the particular amine and which, neither therapeutically nor for any other reason, are objectionable for use in the mouth. Suitable acids of this type are in particular hydrofluoric acid, hydrochloric acid, phosphoric acid, gluconic acid or adipic acid. A particularly preferred amine salt is the dihydrofluoride of the above-mentioned 1,3-diaminopropane.

The unexpected stabilising action of the diamine salts on aqueous solutions of tin(II) salts is shown below for the example of the amine fluoride 297.

EXPERIMENT I

The following are dissolved in distilled water in fluoride concentrations of 100, 250 and 1,000 rpm (calculated as F): Sn(II) fluoride, the amine fluoride 297 and the combination of $SnF_2$ with AmF 297 and with the corresponding amine hydrochloride.

The freshly prepared, clear solutions are stored in an oven at 48° C. and are tested for turbidity and/or precipitation after 1, 4 and 22 hours and after 8 and 20 days. Samples are repeatedly taken from the supernatant liquid of the centrifuged solutions and are used to determine the tin content by atomic absorption spectrophotometry and to determine the fluoride concentration by means of the specific fluoride ion electrode. Each series of experiments was repeated three times. The results are shown in Table I.

EXPERIMENT II

The stability of $SnF_2$ solutions containing amine fluoride 297 and kept in an oven at 48° C. or at room temperature (about 20° C.) was also tested over a period of four weeks by observing the formation of precipitate. The results are shown in Table II.

TABLE I

Occurrence, as a function of time, of a turbidity (x) or of a precipitate (xx), in an oven at 48° C.
(Mean value from 3 experiments; ppm = parts per million)

| Aqueous solution of | Tin content (hours) | | | | Turbidity/Precipitate (Hours and days) | | | | | | Fluoride ion content (Hours) | | | |
|---|---|---|---|---|---|---|---|---|---|---|---|---|---|---|
| | 0 | 1 | 4 | 22 | 0 | 1 | 4 | 22 | 8 | 20 | 0 | 1 | 4 | 22 |
| (1) $SnF_2$ (F = 100 ppm Sn = 312 ppm) | 289 | 281 | 245 | 118 | 0 | 0 | x | xx | xx | xx | 89 | 96 | 85 | 85 |
| (2) AmF 297 (F = 100 ppm) | — | — | — | — | 0 | 0 | 0 | 0 | 0 | 0 | 106 | 105 | 100 | 100 |
| (3) $SnF_2$ + AmF 297 (1:1) (F = 100 ppm Sn = 156 ppm) | 163 | 158 | 163 | 158 | 0 | 0 | 0 | 0 | 0 | 0 | 89 | 88 | 89 | 88 |
| (4) $SnF_2$ + amine hydrochloride* to (2) (1:1) (F = 50 ppm Sn = 156 ppm) | 146 | 146 | 151 | 147 | 0 | 0 | 0 | 0 | 0 | 0 | 45 | 46 | 46 | 40 |
| (5) $SnF_2$ (F = 250 ppm Sn = 780 ppm) | 750 | 730 | 676 | 530 | 0 | 0 | xx | xx | xx | xx | 240 | 240 | 228 | 228 |
| (6) AmF 297 (F = 250 ppm) | — | — | — | — | 0 | 0 | 0 | 0 | 0 | 0 | 253 | 253 | 252 | 250 |
| (7) $SnF_2$ + AmF 297 (1:1) (F = 250 ppm Sn = 390 ppm) | 372 | 371 | 371 | 363 | 0 | 0 | 0 | 0 | 0 | 0 | 230 | 233 | 227 | 229 |
| (8) $SnF_2$ + amine hydrochloride* to (6) (1:1) (F = 125 ppm Sn = 390 ppm) | 386 | 380 | 370 | 375 | 0 | 0 | 0 | 0 | 0 | 0 | 117 | 117 | 118 | 115 |
| (9) $SnF_2$ (F = 1000 ppm Sn = 3123 ppm) | 3075 | 3025 | 2566 | 2515 | 0 | x | xx | xx | xx | xx | 871 | 868 | 798 | 836 |
| (10) AmF 297 (F = 1000 ppm) | — | — | — | — | 0 | 0 | 0 | 0 | 0 | 0 | 1051 | 1050 | 1057 | 1051 |
| (11) $SnF_2$ + AmF 297 (F = 1000 ppm Sn = 1561 ppm) | 1590 | 1630 | 1600 | 1615 | 0 | 0 | 0 | 0 | (x) | (x) | 858 | 858 | 858 | 848 |

*in equimolar amount

TABLE II

Occurrence, as a function of time, of a turbidity (x) or of a precipitate (xx) at room temperature and in an oven at 48° C. (ppm = parts per million)

| Aqueous solution of | Concentration of F⁻ in ppm | pH | Temperature in °C. | Turbidity/Precipitate (Hours and days) | | | | | | | |
|---|---|---|---|---|---|---|---|---|---|---|---|
| | | | | 2 | 20 | 2 | 3 | 7 | 14 | 21 | 28 |
| $SnF_2$ | 250 | 3.5 | about 20 | x | xx | xx | | | | | |
| | | | 48 | x | xx | xx | | | | | |
| $SnF_2$ + AmF 297 | 250 | 4.2 | about 20 | 0 | 0 | 0 | 0 | 0 | 0 | 0 | 0 |
| | | | 48 | 0 | 0 | 0 | 0 | 0 | 0 | 0 | 0 |
| $SnF_2$ | 1000 | 3.4 | about 20 | x | xx | xx | | | | | |
| | | | 48 | x | xx | xx | | | | | |
| $SnF_2$ + AmF 297 | 1000 | 3.9 | about 20 | 0 | 0 | 0 | 0 | 0 | 0 | 0 | 0 |
| | | | 48 | 0 | 0 | 0 | 0 | x | | | |

The stabilising action of the amine fluoride 297 on aqueous solutions of tin(II) fluoride is impressively revealed by Tables I and II. After as little as 1 to 4 hours, SnF2 solutions become turbid, and soon thereafter precipitates form. The combination of the nonprecipitating amine fluoride 297 or amine hydrochloride with tin(II) fluoride, at a fluorine concentration of 50 to 100 ppm, prevents the formation of precipitates from SnF2 for up to 20 days, and does so even at a storage temperature of 48° C. The tin content of the supernatant liquid of centrifuged SnF2 solutions which did not contain any amine salt fell gradually over 22 hours; on the other hand, it remained constant in the combinations SnF2-AmF 297 and SnF2-AmCl. The concentrations of fluoride ions in the supernatant liquids did not change significantly with time (Table I).

The stabilising action of AmF 297 on SnF2 solutions was more pronounced, in the oven experiments, at a fluorine concentration of 250 ppm than at a fluorine concentration of 1000 ppm. At room temperature, neither any turbidity nor precipitates were observable even after 4 weeks (Table II).

The mechanism by which the tin salts are stabilised has not yet been clarified. Possibly it is attributable to the chelation of the tin ions by aliphatic diamines, but the presence of fluoride ions in the tin-amine system also appears to be necessary to achieve stabilisation.

In respect of stabilising action, the mentioned diamine salts sharply contrast with the corresponding salts of monoamines with a long chain fatty alkyl group like, for instance, hexadecylamine (or cetylamine) hydrofluoride. However, monoamine salts of the mentioned kind often have a low solubility in water, which then results in an opalescence of the aqueous solutions. Any opalescence, when already present at the beginning of stability experiments, in practice makes difficult visually evaluating and recording slight turbidity changes. This is, inter alia, also the case with hexadecylamine hydrofluoride.

For this reason, turbidity increase and precipitate formation are best monitored spectrophotometrically at 550 nm. The reaction of hexadecylamine hydrofluoride with stannous fluoride in water has been investigated with this method: the results are shown on the accompanying drawing. At time O, equal parts of a solution of hexadecylamine hydrofluoride in water (250 ppm F) and a solution of SnF2 in water (250 ppm F) are mixed together in the optical cell of a Perkin-Elmer 550 SE spectrophotometer. Within 4 to 5 minutes after mixing, the absorbance at 550 nm raises to a maximum, thus indicating maximal turbidity. During the next 4 to 5 minutes small solid particles coalesce to larger aggregates which, thereafter, start to sediment. Concommitantly the absorbance value decreases to reach the original turbidity level of the hexadecylamine hydrofluoride solution alone (Hex). This level is reached already after 120 to 180 minutes.

This means that all stannous ions which originally were present in the solution have been precipitated after said time. This result strikingly differs form Experiment 7 in Table I (above) where corresponding solutions of SnF2 (250 ppm F) and the diamine hydrofluoride AmF 297 (250 ppm F) even 20 days after mixing do not show any turbidity or precipitate.

The stabilising action of the amine fluoride 297 and of diamine salts in general on aqueous solutions of tin(II) fluoride and of tin salts in general is of practical and commercial importance because it is not accompanied by, say, decreased anti-plaque properties of the tin fluoride or of the amine salt. This has been shown by a clinical investigation of 4 month rinse solutions, the investigation being carried out with the assistance of 16 hygiene students aged from 20 to 26. Four successive rinsing periods each of 10 days were adhered to. Before each of these periods, the teeth of the students were subjected to a professional cleaning and polishing. The students were then instructed to observe meticulously precise mouth hygiene so as to ensure completely sound gums. One of the four rinse solutions shown below was allotted, at random, to each of the volunteers. For each of the rinsing periods, which lasted 10 days, the solutions were prepared once only and were packed in opaque plastic bottles.

The solutions contained:

1. Quinine chloride (500 ppm) and a sweetener—this constituted the placebo solution, for control purposes.
2. SnF2(250 ppm of F−) and the sweetener.
3. N,N,N'-tris-(2-hydroxyethyl)-N'-octadecyl-1,3-diamino-propane dihydrofluoride (AmF 297; 250 ppm of F−) and the sweetener.
4. SnF2 (250 ppm of F−), AmF 297 (250 ppm of F−) and the sweetener. In this solution, the concentration of tin ions and of the amine component of AmF 297 was only half of the concentration in solutions 2 and 3.

During the four rinsing periods, the students rinsed their mouth twice daily for 30 seconds at a time; they were instructed to refrain entirely from brushing their teeth and from other measures aimed at oral hygiene. At the end of each of these rinsing periods, the teeth were cleaned professionally and brushing of the teeth was allowed for 3 days, up to the start of the next rinsing period, for which a different solution was employed.

Accordingly, each of the volunteers carried out the rinsing procedure with all four solutions, on the Latin Square schema. The investigation was carried out double blind.

The rate of plaque formation was determined by the plaque index and was substantiated by standardised colour photographs. The metabolic activity of the plaque was estimated from pH measurements; the plaque collected at the end of each rinsing period was exposed to a 10% by weight strength glucose solution and the change in pH value was measured after 1, 10 and 20 minutes. The gingivitis was determined from the sulcus bleeding index and by measurement of the sulcus fluid (exudate). The results are shown in Table III.

TABLE III

Action of various rinsing solutions on plaque formation, gum-bleeding, gum exudate and pH value of the plaque (mean values ± mean deviation)

| Diagnostic parameter | (1) Control solution | (2) $SnF_2$ (F = 250 ppm Sn = 312 ppm) | (3) AmF 297 (F = 250 ppm) | (4) $SnF_2$ + AmF 297 1:1 (F = 250 ppm Sn = 156 ppm) |
|---|---|---|---|---|
| Plaque index increase | 1.09 ± 0.52 | 1.14 ± 0.51 | 0.88 ± 0.56 | 0.57 ± 0.25*** |
| Plaque pH decrease 1 minute after exposure to glucose | 0.67 ± 0.32 | 0.61 ± 0.39 | 0.30 ± 0.31** | 0.50 ± 0.38 |
| Sulcus bleeding index | 0.35 ± 0.32 | 0.29 ± 0.33 | 0.27 ± 0.40 | 0.21 ± 0.40 |
| Sulcus fluid (exudate) in mm | 3.40 ± 4.70 | 3.09 ± 2.82 | 1.89 ± 2.4 | 1.34 ± 3.16* |

*Significance relative to controls <0.05
**Significance relative to controls <0.01
***Significance relative to controls <0.001

Rinsing with aged $SnF_2$ solution or with amine fluoride 297 alone showed no significant reduction in plaque and was therefore in clear contrast to rinsing with a solution which contained $SnF_2$ and was stabilised with amine fluoride 297; the photographic diagnosis confirmed the results reflected in the plaque index. The achieved reduction in plaque formation was statistically highly significant; the observed potentiation of the plaque-inhibiting action of the two components was entirely unexpected, particularly in view of the low concentrations of tin salts and of amine salt used in the rinsing solutions.

The ability of the dental plaque to form acid from glucose (glycolysis) was only reduced significantly in the case of the rinsing solution containing the amine fluoride.

The diminished gingivitis, determined from the sulcus bleeding index and the measurement of the gum exudates proved to be greatest for the mouthwash containing $SnF_2$ and AmF 297, and was less pronounced, and statistically not significant, for the rinsing solutions containing $SnF_2$ or AmF 297 alone.

Overall, the experiment with young adults showed that the diamine salts stabilise aqueous solutions of tin-(II) fluoride effectively and that at the same time the anti-plaque action of $SnF_2$ and its advantageous action against gingivitis remain fully preserved or are even emphatically potentiated.

In practical implementation, that is to say in the manufacture or ready-to-use formulations, containing all conventional additives, for the care of the mouth and the teeth, it was furthermore found that the addition, as a solubilising agent and emulsifier, of at least one non-ionic, water-soluble addition product of ethylene oxide effected an ultimate improvement in respect of the stabilisation of the tin salts. The products concerned are polyethers, particularly alkylphenol polyglycol ethers and further products resulting from the oxyethylation of fatty acids, fatty acid amides, fatty amines and fatty alcohols.

Well-known examples of this group of compounds are the products sold under the trademark Cremophor RH by Messrs. Badische Anilin- und Sodafabrik, Ludwigshafen am Rhein (Federal Republic of Germany). These products are prepared by reacting, for example, about 40 or about 60 mols of ethylene oxide with 1 mol of hydrogenated castor oil. The main constituents of the Cremophor RH products are, accordingly, esters of hydrogenated castor oil fatty acids with oxyethylated glycerol. In addition, they contain polyglycol esters of the hydrogenated castor oil fatty acids, as well as free oxyethylated glycerol and higher polyethylene glycols. The secondary OH groups of the hydroxystearic acid esters can in part be esterified with another molecule of hydroxystearic acid. Oxyethylation of the secondary OH groups of the hydroxystearic acid molecules takes place only to a very slight extent.

Other known examples of suitable addition products of ethylene oxide are the products Brij (R) and Tween (R) from Messrs. ICI America Inc., Atlas Chemicals Div., Wilmington (DE, USA) as well as the products Pluronic (R) from Messrs. Wyandotte Chemicals Co., Wyandotte (MI, USA). Within these products, Tween 20, 40, 60 and 80 and Pluronic F-68 are preferred.

Parallel series of experiments were carried out with mouth rinse solutions which contained 0.1% by weight of the emulsifier Cremophor RH and which, after preparation, were stored for 10 days at room temperature of at 40° C. After this period of time, the stabilising action was determined by visual assessment of the appearance.

The basic composition of each rinse solution was as follows:

| | |
|---|---|
| Ariavite Blue 385, 0.2% by weight strength (dyestuff) | 1.0 g |
| Ethanol | 50.0 g |
| Flavourings | 1.2 g |
| Emulsifier, Cremophor RH 40 or 60 | 1.0 g |
| Demineralised water, to make up to | 1,000.0 g |

The content of active substances in each solution is shown in the table below.

TABLE IV

| Experiment 1 | Experiment 2 |
|---|---|
| $SnF_2$, alone | $SnF_2$, as in |
| 50 ppm of $F^-$ | Experiment 1 + |
| 100 ppm of $F^-$ | AmF 297 |
| 250 ppm of $F^-$ | in each case |
| | 50 ppm of $F^-$ |

After 10 days, the three solutions of experiment 1 showed a slight but noticeable flocculent precipitate, whether they had been stored at room temperature or at 40° C.; the supernatant liquids all showed a slight turbidity. With increasing SnF$_2$ concentration, a more pronounced discoloration of the solution became noticeable. In contrast thereto, all the solutions of experiment 2 could be described as clear.

It can be seen from this that the emulsifier alone does not stabilise the tin fluoride, whilst on the other hand the combination of the amine salt and the emulsifier produces complete stabilisation of the tin (II) salt in a ready-to-use mouth rinse solution. No differences in action between the rinse solutions stored at room temperature and those stored at 40° C. was detectable.

In the examples which follow, the numerical data relate to parts by weight; percents are also by weight.

The mouthwashes according to Examples 1 to 5, 10 and 11 are ready-to-use rinse solutions which have not to be diluted.

EXAMPLE 1:

Mouthwash

| | |
|---|---|
| N,N,N'—tris-(2-Hydroxyethyl)-N'—octadecyl-1,3-diaminopropane dihydrofluoride | 0.14 (=0.01% of F$^-$) |
| Tin(II) fluoride | 0.04 (=0.01% of F$^-$) |
| Glycerol | 10.0 |
| Ethanol | 16.5 |
| Cremophor RH 40 | 0.10 |
| Saccharin and flavourings | 0.145 |
| Water to make up to | 100.0 |

EXAMPLE 2:

Mouthwash

| | |
|---|---|
| N,N,N'—tris-(2-Hydroxyethyl)-N'—octadecyl-1,3-diaminopropane dihydrofluoride | 0.2 |
| Tin(II) fluoride | 0.1 |
| Glycerol | 10.0 |
| Flavourings | 0.145 |
| Water to make up to | 100.0 |

EXAMPLE 3:

Toothpaste

| | |
|---|---|
| N,N,N'—tris-(2-Hydroxyethyl)-N'—octadecyl-1,3-diaminopropane dihydrochloride | 1.0 |
| Tin(II) fluoride | 0.2 |
| Sodium fluoride | 0.1 |
| Guar gum | 1.5 |
| Silica | 16.0 |
| Flavourings and sweetener | 1.5 |
| Water to make up to | 100.0 |

EXAMPLE 4:

Dental GEL

| | |
|---|---|
| Hydroxyethylcellulose (Natrosol 250) | 3.0 |
| N,N,N'—tris-(2-Hydroxyethyl)-N'—octadecyl-1,3-diaminopropane dihydrofluoride | 1.25 |
| Tin(II) fluoride | 0.08 |
| Pluronic F-68 | 1.5 |
| Flavourings and dyestuffs | 0.5 |
| Water to make up to | 100.0 |

What is claimed is:

1. A process for stabilizing an oral composition consisting essentially of water and at least one tin (II) salt selected from the group consisting of tin (II) fluoride and a mixture of a fluorine-free tin (II) salt and sodium fluoride, which comprises the step of treating said composition with a cationic surfactant diamine salt in an amount effective to stabilize the tin (II) salt, the diamine moiety being selected from the group consisting of compounds of the formula:

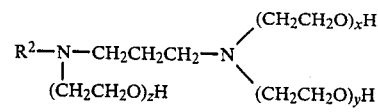

where R$^2$ denotes a fatty alkyl group with 7 to 19 carbon atoms and x, y and z each denotes an integer from 1 to 10.

2. A process according to claim 1, which comprises additionally treating said composition, for further stabilization and simultaneously as a non-ionic solubilizing agent and emulsifier, with at least one non-ionic, water-soluble addition product of ethylene oxide.

3. A process according to claim 2, wherein the addition product of ethylene oxide is a polyether selected from the group consisting of alkylphenol polyglycol ethers and other products resulting from the oxyethylation of fatty acids, fatty acid amides, fatty amines and fatty alcohols.

4. A process according to claim 1, wherein the acid moiety of the diamine salt is selected from hydrofluoric acid, hydrochloric acid, phosphoric acid, gluconic acid and adipic acid.

5. A process according to claim 1, wherein the diamine salt is a salt of N,N,N'-tris-(2-hydroxy ethyl)-N'-octadecyl-1,3-diaminopropane.

6. A process according to claim 1, wherein said composition is in an orally applicable form selected from toothpastes, dental gels, mouthwashes, mouth sprays, prophylaxis pastes and solutions for topical application.

* * * * *